US012697502B2

(12) United States Patent
Sheltraw et al.

(10) Patent No.: US 12,697,502 B2
(45) Date of Patent: Aug. 4, 2026

(54) KILOHERTZ TRANSCRANIAL MAGNETIC PERTURBATION WITH TEMPORAL INTERFERENCE

(71) Applicant: THE REGENTS OF THE UNIVERSITY OF CALIFORNIA, Oakland, CA (US)

(72) Inventors: Daniel J. Sheltraw, Albany, CA (US); Benjamin A. Inglis, Lafayette, CA (US); Richard Irwin Ivry, El Cerrito, CA (US); Ludovica Labruna, Kensington, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 953 days.

(21) Appl. No.: 17/921,563

(22) PCT Filed: Apr. 27, 2021

(86) PCT No.: PCT/US2021/029311
§ 371 (c)(1),
(2) Date: Oct. 26, 2022

(87) PCT Pub. No.: WO2021/222185
PCT Pub. Date: Nov. 4, 2021

(65) Prior Publication Data
US 2023/0158321 A1      May 25, 2023

Related U.S. Application Data

(60) Provisional application No. 63/016,705, filed on Apr. 28, 2020.

(51) Int. Cl.
*A61N 2/00* (2006.01)
*A61N 1/40* (2006.01)
*A61N 2/02* (2006.01)

(52) U.S. Cl.
CPC ............... *A61N 2/006* (2013.01); *A61N 1/40* (2013.01); *A61N 2/02* (2013.01)

(58) Field of Classification Search
CPC .................................................. A61N 2/00–12
See application file for complete search history.

(56) References Cited

U.S. PATENT DOCUMENTS

2006/0199992 A1      9/2006   Eisenberg et al.
2009/0018384 A1*     1/2009   Boyden .................... A61N 2/02
                                                            600/13

(Continued)

FOREIGN PATENT DOCUMENTS

WO          2020123154          6/2020

OTHER PUBLICATIONS

International Search Report and Written Opinion, PCT/US2021/029311, Aug. 24, 2021, 9 pages.

(Continued)

*Primary Examiner* — Thaddeus B Cox
(74) *Attorney, Agent, or Firm* — Miller Nash LLP

(57)          ABSTRACT

A magnetic stimulation system has at least two magnetic coils, each coil to generate an induced electric field of a magnitude having a desired effect on a brain, at least two frequency controllers, wherein each coil is electrically connected to a corresponding frequency controller, the frequency controllers to adjust a frequency of power supplied to the corresponding coils according to a desired interference pattern, and at least one power source to provide power to the frequency controllers corresponding to each coil. A method of operating a magnetic stimulation system includes generating two or more signals to apply to two or more coils, each signal corresponding to one of the at least two coils, wherein at least two coils receive different signals and the (Continued)

different signals differ at least in frequency according to a desired temporal interference pattern.

12 Claims, 4 Drawing Sheets

(56) References Cited

U.S. PATENT DOCUMENTS

| | | |
|---|---|---|
| 2011/0245708 A1 | 10/2011 | Finkel et al. |
| 2013/0066395 A1 | 3/2013 | Simon et al. |
| 2014/0371515 A1 | 12/2014 | John |
| 2017/0106202 A1 | 4/2017 | Butinar et al. |
| 2018/0353283 A1 | 12/2018 | Casse et al. |
| 2019/0030357 A1 | 1/2019 | Xie |

OTHER PUBLICATIONS

Cantarero et al., Celebellar Direct Current Stimulation Enhances On-Line Motor Skill Acquisition through an Effect on Accuracy, J. Neuroscience, 35(7):3285-3290, Feb. 18, 2015.

Chaieb et al., "Transcranial alternating current stimultion in the low kHz range increases motor cortex excitability," Restorative Neurology and Neuroscience, 29, pp. 167-175 (2011).

Chaieb et al., "Safety of 5 kHz tACS," Brain Stimulation, 7, pp. 92-96 (2014).

Chhatbar et al., "Safety and tolerability of transcranial direct current stimulation to stroke patients—A phase I current escalation study," Brain Stimulation 10 (2017 553-559.

Conson et al., "Transcranial Electrical Stimulation over Dorsolateral Prefrontal Cortex Modulates Processing of Social Cognitive and Affective Information," PLOS One, May 7, 2015, 14 pages.

Deng et al., "Electric field depth-focality tradeoff in transcranial magnetic stimulatoin: simulation comparison of 50 coil designs," Brain Stimulation, 6(1), Jan. 2013, 13 pages.

Fava et al., Double-bind, proof-of-concept (POC) trial of Low-Field Magnetic Stimulation (LFMS) augmentation of antidepressant therapy in treatment-resistant depression (TRD), Brain Stimulation 11, (2018) 75-84.

Galea et al., "Dissociating the Roles of the Cerebellum and Motor Cortex during Adaptive Learning: The Motor Cortex Retains What the Cerebellum Learns," Cerebral Cortex, 21, pp. 1761-1770, Aug. 2011.

Giglia et al., "Anodal transcranial direct current stimulation of the right dorsolateral prefrontal cortex enhances memory-guided responses in a visuospatial working memory task," Functional Neurology, 29(3), pp. 189-193 (2014).

Heimrath et al., "Modulation of pre-attentive spectro-temporal feature processing in the human auditory systems by HD-tDCS," European J. Neuroscience, 41, pp. 1580-1586 (2015).

Hordacre et al., "Variability in neural excitability and plasticity induction in the human cortex: A brain stimulation study," Brain Stimulation 10, pp. 588-595 (2017).

Horvath et al., "No significant effect of transcranial direct current stimulation (tDCS) found on simple motor reaction time comparing 15 different simulation protocols," Neurospychologia, 91, pp. 544-552 (2016).

Hsu et al., "Effects of noninvasive brain stimulation on cognitive function in healthy aging and Alzheimer's disease: a systematic review and meta-analysis," Neurobiology of Aging 36, pp. 2348-2359 (2015).

Huang et al., "Measurements and models of electric fields in the in vivo human brain during transcranial electric stimulation," eLife Sciences, 6:e18834, pp. 1-26, Feb. 7, 2017.

Wostmann et al., "Opposite effects of lateralised transcranial alpha versus gamma stimulation on auditory spatial attention," Brain Stimulation, 11, pp. 752-758 (2018).

Javadi et al., "Oscillatory Reinstatement Enhances Declarative Memory," J. Neuroscience, 37:41, pp. 9939-9944, Oct. 11, 2017.

Koops et al., "Transcranial direct current stimulation as a treatment for auditory hallucinations," Frontiers in Psychology, 6:244, Mar. 6, 2015, 6 pages.

Kunz et al., "5kHz Transcranial Alternating Current Stimulations: Lack of Cortical Excitability Changes when Grouped in a Theta Burst Pattern," Frontiers in Human Neuroscience, 10:683, Jan. 10, 2017, 8 pages.

Li et al., "Clinical utility of brain stimulation modalities following traumatic brain injury: current evidence, Neuropsychiatric Disease and Treatment," J. Neuropsychiatric Disease and Treatment, 5:11, pp. 1573-1586, Jun. 30, 2015.

Meinzer, "Transcranial direct current stimulation of the primary motor cortex improves word-retrieval in older adults," Frontiers in Aging Neuroscience, 6:253, Sep. 23, 2014, 9 pp.

Mondino et al., "Can transcranial direct current stimulation ((DCS) alleviate symptoms and improve cognition in psychiatric disorders? ", J. Biological Psychiatry, 15, pp. 261-275, 2014.

Huang et al., "Plascity induced by non-invasive transcranial brain stimulation: a position paper," Clinical Neurophysiology, 128, pp. 2318-2329 (2017).

Nevler and Ash, "TMS as a Tool for Examining Cognitive Processing," Current Neurology Rep, 15:52, (2015), 11 pages.

Nitsche and Paulus, "Excitablity changes induced in the human motor cortex by weak transcranial direct current stimulation," J. Physiology, 527:3, pp. I633-I639 (2000).

Peterchev et al., "Fundamentals of transcranial electric and magnetic stimulation dose: definition, selection, and reporting practices," Brain Stimulation, 5, pp. 435-453 (2012).

Reis et al., "Supporting Information," PNAS.0805413106, 10:1073, 6 pages.

Richmond et al., "Transcranial Direct Current Stimulation Ehances Verbal Working Memory Training Performance over Time and Near Transfer Outcomes," J. Cognitive Neuroscience, 26:11, pp. 2443-2454 (2014).

Mondino et al., "Can transcranial direct current stimulation (tDCS) alleviate symptoms and improve cognition in psychiatric disorders? ", J. Biological Psychiatry, 15, pp. 261-275, 2014.

Reis et al., "Noninvasive cortical stimulation enhances motor skill acquisition over multiple days through an effect on consolidation," PNAS, 106:5, Feb. 3, 2009, pp. 1590-1595.

Huang et al., Plasticity induced by non-invasive transcranial brain stimulation: A position paper, Clinical Neurophysiology, 128 (2017) 2318-2329.

* cited by examiner

KILOHERTZ TRANSCRANIAL MAGNETIC PERTURBATION WITH TEMPORAL INTERFERENCE

RELATED APPLICATIONS

This application is a 371 of International Application No. PCT/US2021/029311, filed Apr. 27, 2021, which claims priority to and the benefit of US Provisional Application No. 63/016,705, filed Apr. 28, 2020, which are incorporated by reference herein in their entirety.

STATEMENT REGARDING FEDERALLY SPONSORED RESEARCH AND DEVELOPMENT

This invention was made with government support under Grant Number EB028075 awarded by the National Institutes of Health, and under Grant Number 1946316 awarded by the National Science Foundation. The government has certain rights in the invention.

TECHNICAL FIELD

This disclosure relates to transcranial perturbation, more particularly to kilohertz transcranial magnetic perturbation (kTMP).

BACKGROUND

Researchers use a range of methods to understand and manipulate brain function. On the observational end, sophisticated methods have been developed to measure neural activity at a broad range of scales. In research with human participants, non-invasive techniques such as electroencephalography (EEG) and functional magnetic resonance imaging (fMRI) can measure neural activity as the participants perceive stimuli, make decisions, or interact with the environment. These observational techniques are important tools for developing theories describing the functional organization of the many components of the human brain.

Since their emergence in the 1980s, non-invasive brain stimulation (NIBS) methods have provided an approach to modulate activity in targeted brain regions. Broadly speaking there are two types of electromagnetic NIBS systems presently: transcranial magnetic stimulation (TMS) and transcranial electrical stimulation (TES). Both methods couple to the targeted brain region through the electric fields (E-fields) they produce. TES produces its electric field by injecting a current through the skull by means of electrodes placed on the scalp. TMS, on the other hand, produces its electric field through space by means of magnetic induction due to a current-carrying coil placed near the scalp. The spatial extent of the neural perturbation depends on the configuration of the stimulating device. With TMS the perturbation impacts a brain volume of under 1 cm³; the resolution is generally poorer with TES methods, although new high density systems have the potential to approach the resolution of TMS.

The electric fields induced by NIBS may be categorized as subthreshold or suprathreshold. Suprathreshold fields are strong enough to cause immediate action potentials in targeted neurons whereas subthreshold fields are not. In terms of cortical impact, suprathreshold E-fields directly elicit action potentials and are safely possible only with perturbation via magnetic fields. Subthreshold E-fields do not produce action potentials but can instead alter the excitability state of the targeted neurons. The electric fields of TMS and TES, whether suprathreshold or subthreshold, are used to produce transient changes in neural activity that allow researchers to ask how the behavior of neurologically healthy individuals is affected by the targeted perturbation.

For example, a short train of subthreshold TMS pulses over the inferior frontal cortex, in other words Broca's area, will disrupt the ability of a person to speak and allows researchers to test the importance of speech production in language comprehension. The effects of TES electric fields, which in humans are always subthreshold for reasons of safety, are more nuanced, since this form of stimulation does not directly activate neurons. Rather, it produces a change in the state of excitability of the targeted brain region, with the change being an increase or decrease in excitability depending upon the amplitude, direction and frequency of the electric field in the targeted region. By applying the current for an extended period, the change in the state of excitability can alter brain function, and thus either interfere with or enhance behavior. These changes, albeit transient, can persist beyond the duration of the applied electric field, indicating that the underlying mechanisms involve temporary structural changes to the brain tissue.

In addition to their widespread application in the study of brain function, NIBS methods have been recognized for their potential for neuro-rehabilitation, as well as in the treatment of psychiatric disorders. For example, in individuals with hemiparesis from stroke, TMS can be used to directly activate neurons in the motor cortex, helping the patient learn to produce movement from residual neural tissue. Alternatively, TES can be used to increase the state of excitability, facilitating the neural changes that occur during learning. For the past decade, the potential of TMS for treating patients with psychiatric disorders such as depression, mood disorders, especially patients who respond poorly to common drug therapies, has been investigated in clinical trials, with similar trials coming on line for TES. A limitation of TMS is that it cannot produce an electric field to a target region deep in the brain without also producing an even larger electric field in the superficial brain tissue. Extrema cannot be produced in electromagnetism, the field amplitudes fall off with the inverse of radial distance.

DETAILED DESCRIPTION OF THE EMBODIMENTS

The embodiments here result in neuronal perturbation by one or more continuous time varying electric fields produced using magnetic induction. kTMP refers to kilohertz transcranial magnetic perturbation. The kTMP system is designed to operate in the subthreshold space of electric fields.

This discussion will refer to the kTMP system as kTMP or more generally TMP, and the TES system as a transcranial electric perturbation (TEP) system. TMP uses a time varying current within coils external and not in electrical contact with the head. The electric contact method TEP uses a source of current and electrodes in contact with the head to produce an electric field within the brain. The electric field within the head cannot contain extreme values, they generally exist on the boundaries of the head, that is, at the scalp surface.

Figure 1:
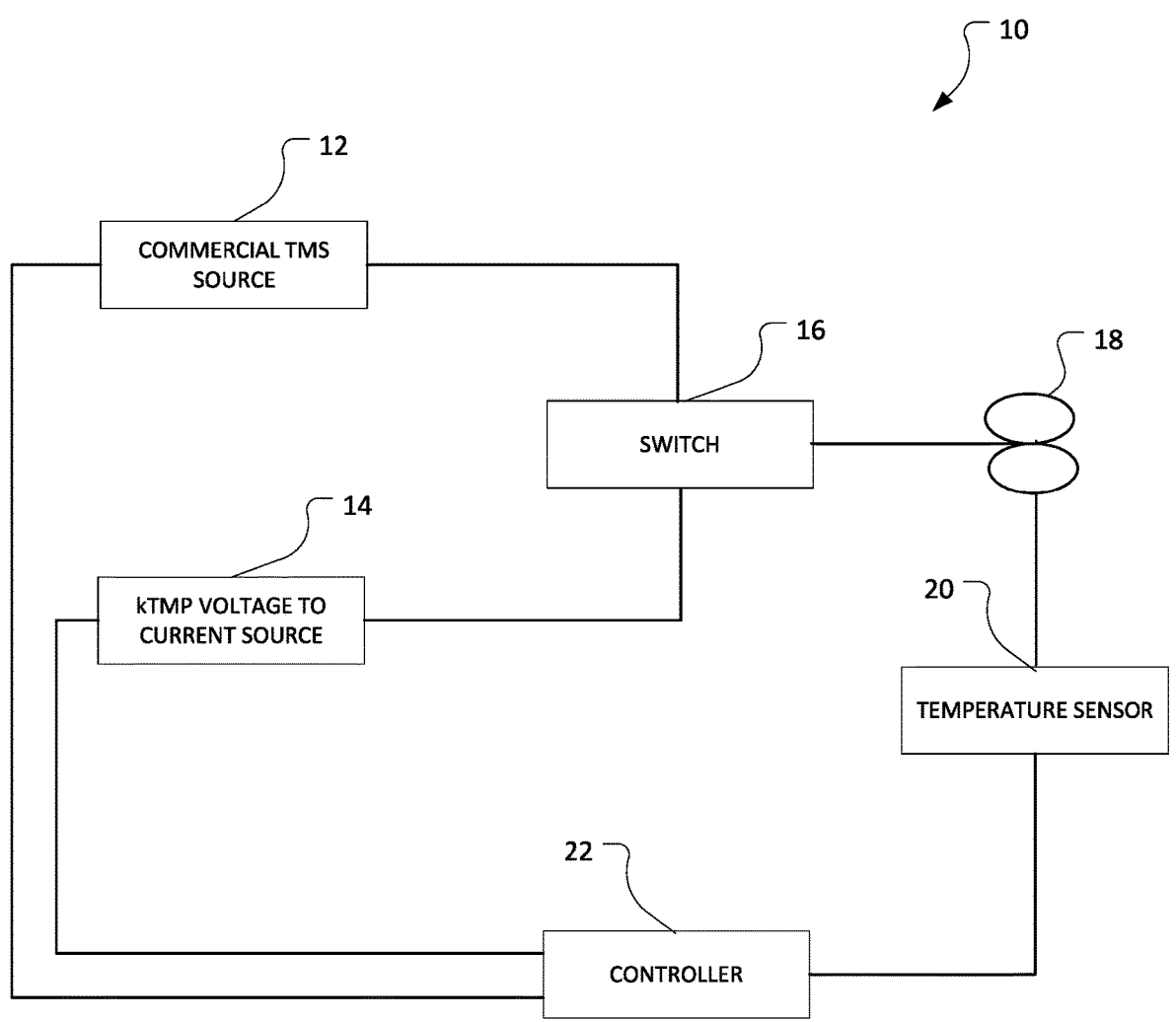
FIG. 1 shows an embodiment of a single coil kilohertz transcranial magnetic perturbation system.

The kTMP system induces a continuous time varying electric field, in contrast to the pulsed electric fields produced from extant TMS systems. By using continuous high frequency magnetic fields, the kTMP system substantially increases the dynamic range of the applied perturbation relative to TEP methods. When delivered with a TMS coil, kTMP maintains the spatial response of TMS. FIG. 1 shows an example of a kTMP system as set out in PCT patent application PCT/US19/63514, which is incorporated in its entirety here.

If desired, the same coil can also be used to deliver suprathreshold perturbation by switching to a TMS delivery system.

FIG. 1 shows an embodiment of a kTMP system 10. The construction of the kTMP system may entail a combination of commercial and customized components. One embodiment includes a commercial TMS coil 18 driven by a voltage-to-current amplifier 14 capable of delivering up to 200 A of current to the load, with sufficient compliance voltage, and having a carrier frequency of 0.5-10 kHz. The coil will produce a magnetic field that in turn induces the desired electric field. One embodiment of the control system will allow the researcher to choose the carrier frequency, amplitude, amplitude modulation, and duration of the kTMP waveforms. Other embodiments of the control system may include the option for frequency modulation as well.

For ease of experimentation, programmable solid-state switching 16 will allow the TMS coil to be driven by either a kTMP unit or a commercially available TMS unit 12 in sequential manner. The commercial TMS unit is not part of the kTMP system. However, it can be connected to the TMS coil in conjunction with the kTMP system and used to elicit MEPs (Motor Evoked Potentials), allowing assessment of changes in neural excitability induced by the kTMP system. The voltage to current source 14 can be controlled to apply a continuous, rather than a pulsed field, in the coil.

In one embodiment, the control hardware will comprise a multifunction I/O Board combined with a desktop PC. This control system 22 will provide the kTMP voltage-to-current amplifier 14 with the analog voltage signal specifying the desired kTMP waveform, electronic control of the source switch 16, and may provide a real-time graphical display of the ongoing perturbation waveform and protocol on a separate display (not shown) or as part of the controller. The switch allows selection between the sources 12 and 14.

The terms controller or processor as used herein include microprocessors, microcomputers, Application Specific Integrated Circuits (ASICs), cloud-based servers, and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a non-transitory computer readable medium such as a hard disk, optical disk, removable storage media, solid-state memory, Random Access Memory (RAM), etc.

As will be appreciated by one of skill in the art, the functionality of the program modules may be combined or distributed as desired in various aspects. In addition, the functionality may exist in whole or in part in firmware or hardware equivalents such as integrated circuits, FPGAs (field programmable gate arrays), and the like. Particular data structures may be used to more effectively implement one or more aspects of the disclosure, and such data structures are contemplated within the scope of computer executable instructions and computer-usable data described herein.

With kTMP, one can produce subthreshold kHz E-fields with an order of magnitude greater amplitude than TES/TEP variant. An issue that arises with TEP results from having the electrodes in contact with the scalp. The discussion now considers safety and efficacy of the E-fields produced by the kTMP system, relative to other NIBS approaches. For a given cortical E-field amplitude, TES/TEP is associated with a much larger scalp electric current density than TMS. As such, safety issues regarding scalp heating and comfort impose a critical limit on the maximum amplitude of TES/TEP-induced cortical E-fields.

Recent estimates of the cortical E-field induced by 1.0 mA tES in humans range from 0.17 V/m (Voroslakos et al., 2018) to 0.38 V/m (Huang et al., 2018). Given that almost all studies to date have been conducted at 1 or 2 mA, the maximum induced E-fields would reach somewhere between 0.17 V/m and 0.76 V/m. One recent study indicates that people can tolerate a 4 mA current (Chhatbar et al., 2017), but this intensity is problematic given that participants are likely to easily discriminate real from sham stimulation (unlike at lower stimulation levels).

TMS and kTMP entail much lower scalp E-fields than TES to achieve the same cortical E-field amplitude. As such, standard, TMS might appear to offer an alternative method to induce a continuous wave E-field of greater amplitude than possible with standard tACS up to 250 Hz, transcranial Alternating Current Stimulation (tACS), without the safety concerns about scalp burns and pain. However, this is not practically possible. Achieving continuous E-fields down to the TES frequency range, as low as tens to hundreds of Hz, would require extreme current in the TMS coil, introducing severe power and coil heating problems. Nonetheless, in principle a train of subthreshold TMS pulses could be used to induce cortical E-field amplitudes that exceed the range of TEP methods. A train of TMS pulses at some rate does not produce a single frequency response at that rate but a spectrum comprising numerous peaks of E-field amplitude, the largest of which is at the TMS system carrier frequency. Frequency specificity is not possible with pulsed TMS.

Using a single coil, the kTMP controller can apply amplitude modulation of current in the coil at lower frequency that allows for TMP to induce the desired E-fields, creating low frequency beat patterns in the high carrier frequency current.

Figure 2:
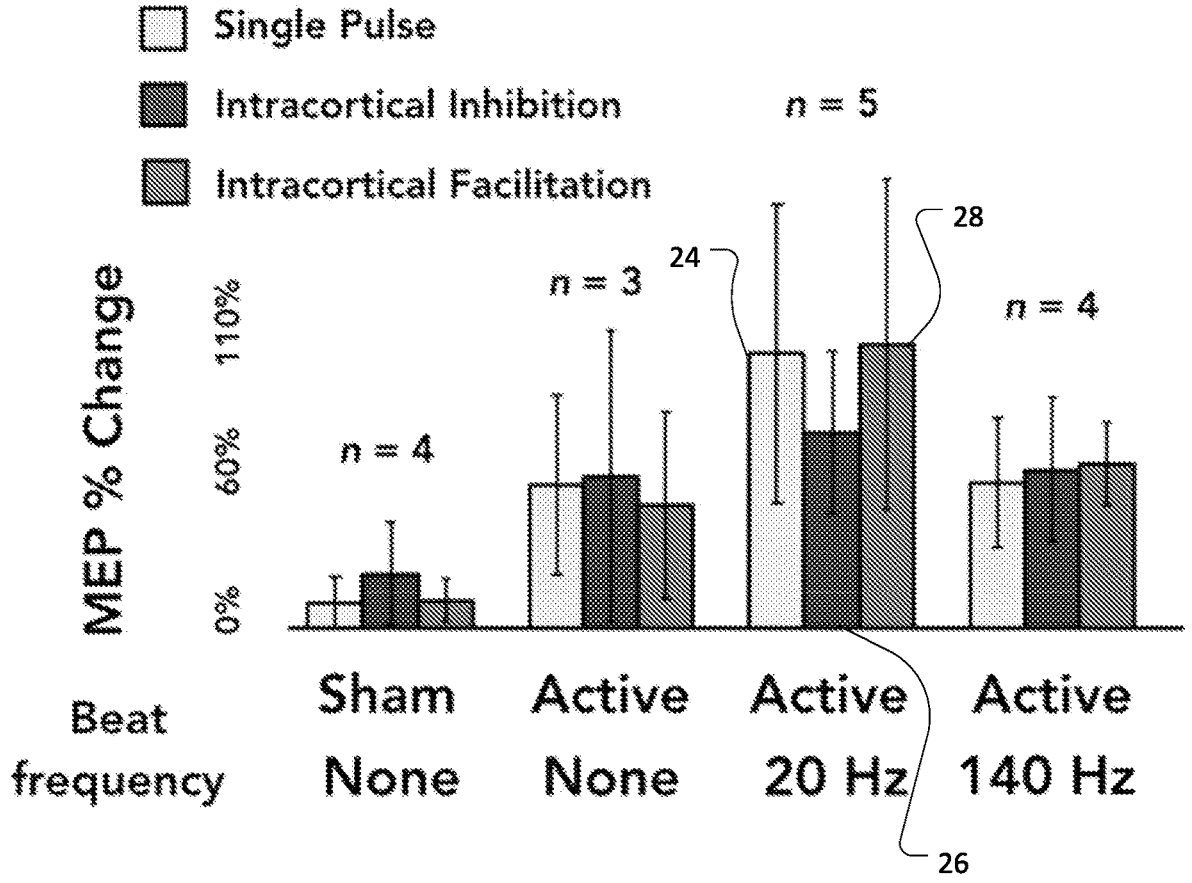
FIG. 2 shows data obtained with an embodiment of a single coil kilohertz transcranial magnetic perturbation system using optional amplitude modulation.

FIG. 2 shows pilot data demonstrating that the kTMP can employ amplitude modulation on cortical excitability. This offers a way to stimulate at physiologically relevant frequencies, allowing kTMP to work in a manner similar to tACS but at much higher E-field strength. The procedure used to gather the data set the carrier frequency at 3.5 kHz, and used amplitude modulation to create beat frequencies of 20 Hz and 140 Hz. Two non-modulated conditions were also included, both non-modulated with a 3.5 kHz input signal, one set to produce a cortical E-field of 2 V/m, shows as the "Active" case in FIG. 2, and one 0.01 V/m, referred to as "Sham" in FIG. 2. The parameters for the amplitude modulation were set to produce a 2 V/m E-filed at the cortical surface.

In the experiments that resulted in the data represented in FIG. 2, three participants completed all four conditions, and two others completed a subset of the conditions. Each condition required a 2-hour session with a minimum of three days between sessions. The experiment measured the MEPs before and after kTMP with single and paired-pulse TMS assays, collecting data from 30 trials for each measure in each of five assessment blocks. The data was averaged across the three post-stimulation assessment blocks. The results are presented in terms of the percent change, related to the two pre-stimulation assessment blocks.

The results have several promising indicators. First, the non-modulated condition produced an increase of approximately 53% of the three different probes of cortical excitability over the sham condition. Second, the results show an increase of excitability in the two amplitude modulated conditions. The 20 Hz amplitude modulated condition has a quite marked increase in line with tACS literature. The single-pulse TMS probe shown as the lightest bar such as 24 in FIG. 2, has amplitudes of MEPs 95% greater than that observed in the sham condition, and 50% greater than that observed in the non-modulated active condition. The darkest bars such as 26 represents intracortical inhibition, and the middle shaded bars such as 28 show the intracortical facilitation.

In addition to the increased capability of amplitude modulation, frequency modulation could add further capabilities to the system. This may provide advantages in simplifying the system, and increasing the operational range of the system. The embodiments here can also produce a focal perturbation using the concept of temporal interference. The discussion here refers to these embodiments as kTMP with temporal interference, kTMP-TI. The embodiments here use kTMP-TI and employ two or more coils.

In the simplest example of a two-coil system, each coil is supplied with a separate sinusoidal current at a slightly different frequency. If, for example, the system drives the first coil at 2 kHz and the second coil at 2.01 kHz, in the region that experiences the magnetic fields of both coils there will be a temporal interference effect at the difference of the two drive frequencies, in this example at 10 Hz. This is merely one example. The relevant measure lies in the difference between the two frequencies. For example, if the carrier, or base, frequency is 1.4 kHz, the different between the two coil frequencies may differ based upon a percentage of the carrier frequency. For example, if one coil operates at 1.4 KHz, the other may vary by 10% of that or by 140 Hz. The difference in frequencies has the most effect on the temporal interference pattern and the perturbation.

The system then produces a focal response in the brain at the temporal interference frequency by aligning the two coils' induced electric fields relative to each other in an appropriate manner, even though the induced electric fields at the carrier frequencies are greater nearer to the respective coils. The temporal interference phenomenon has been used in several domains previously, most recently in the context of direct electrical stimulation using pairs of electrodes as disclosed in U.S. Pat. No. 10,173,061.

Figure 3:
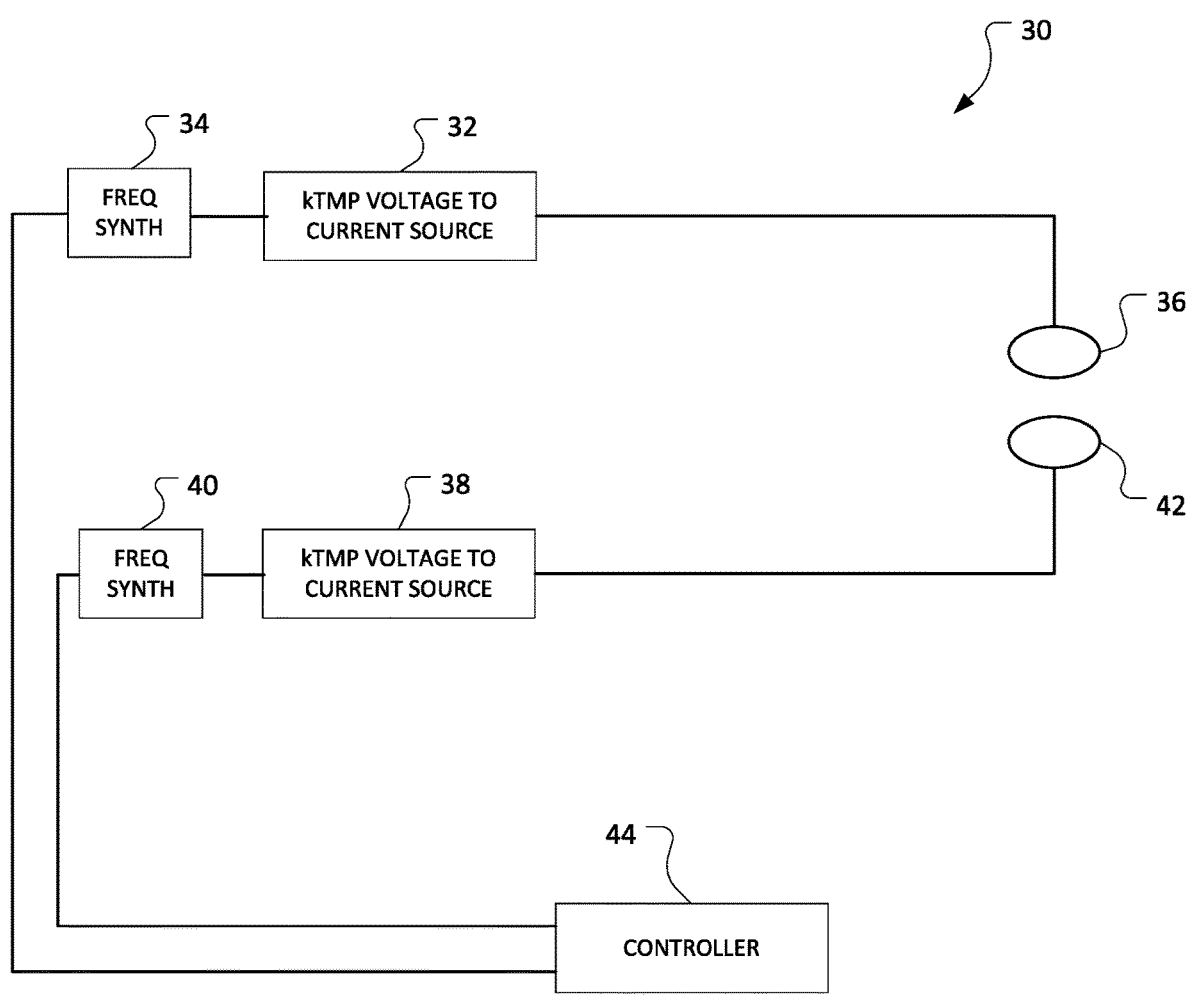
FIG. 3 shows an embodiment of a kilohertz transcranial magnetic perturbation, temporal interference system.

FIG. 3 shows an embodiment of a kTMP-TI system. The kTMP-TI system 30 will feature at least two independently driven and spatio-temporally interfering coils 36 and 42. The shape and size of the coils is not limited. Coils may be circular, figure-8 or any shape appropriate to achieve the desired focal response deep in the brain, and they are not required to be a pair of the same shape. Similarly, there may be more than 2 coils, such as 3 or 5 coils, or even more. The kTMP voltage to current sources 32 and 38 in this embodiment each correspond to, or are dedicated to, one coil. However, in other configurations it is possible to use one current source for both coils. The controller 44 determines the nature of the waveforms and their frequencies to manage the offset patterns to generate the desired interference frequency. The controller may use frequency synthesizers such as 34 and 40 as frequency controllers to control the voltage to current sources, which may consist of amplifiers. The controller may also control one frequency synthesizer to adjust the frequencies for each coil. If desired, the controller can also switch between the kTMP-TI system and a commercial TMS system connected to one or more of the coils, such as for the standard kTMP system shown in FIG. 1.

As mentioned above, the addition of a second coil may improve the focality of the neuronally active electric field compared to the single coil kTMP system. A complicating factor in the use of one coil lies in adjusting the position of the focal response, which is the location at which the field causes the perturbation in the brain. Adjusting the position of the coil may require a system that allows the coil to move to achieve the target location stimulation. With two coils, the need to move the coil may be reduced because the current to each coil can be adjusted separately through controller board 44, allowing for some spatial control of the brain response. The controller may be configurable to provide amplitude modulation, frequency modulation, or both.

The kTMP-TI system will open up a new experimental space of E-field interaction within the human brain in three significant ways. First, the system has spatial localization of amplitude modulation. The coupled system will enable targeting of deep brain regions with specific amplitude modulated waveforms, a challenge with current TMS and tES systems. Second, the system has a significant increase in subthreshold E-field strength. The kTMP of the system of FIG. 1 may induce E-fields of varying V/m levels depending upon the frequency (0.5-10.0 kHz). The limits are defined only by the amplifier limits and the coil cooling capacity. This allows for increases of at least an order of magnitude over the maximum possible with continuous tES systems due to comfort/safety concerns. The kTMP-TI system will be capable of delivering E-fields up to the amplifier and cooling capacities of the system. Third, the system allows for closed-loop interaction between kTMP and brain monitoring, such as with an EEG system. The system will be capable of interacting, in real-time, with simultaneously acquired EEG data to refine the kTMP signal to provide the most effective local E-field amplitude and waveform for eliciting EEG changes of interest.

The embodiments here differ substantially and are likely safer and produce greater electric field amplitudes in brain tissue than using direct electrical contact. Furthermore, the spatial properties of kTMP-TI would make it operate differently to 'standard' single coil kTMP.

Figure 4:
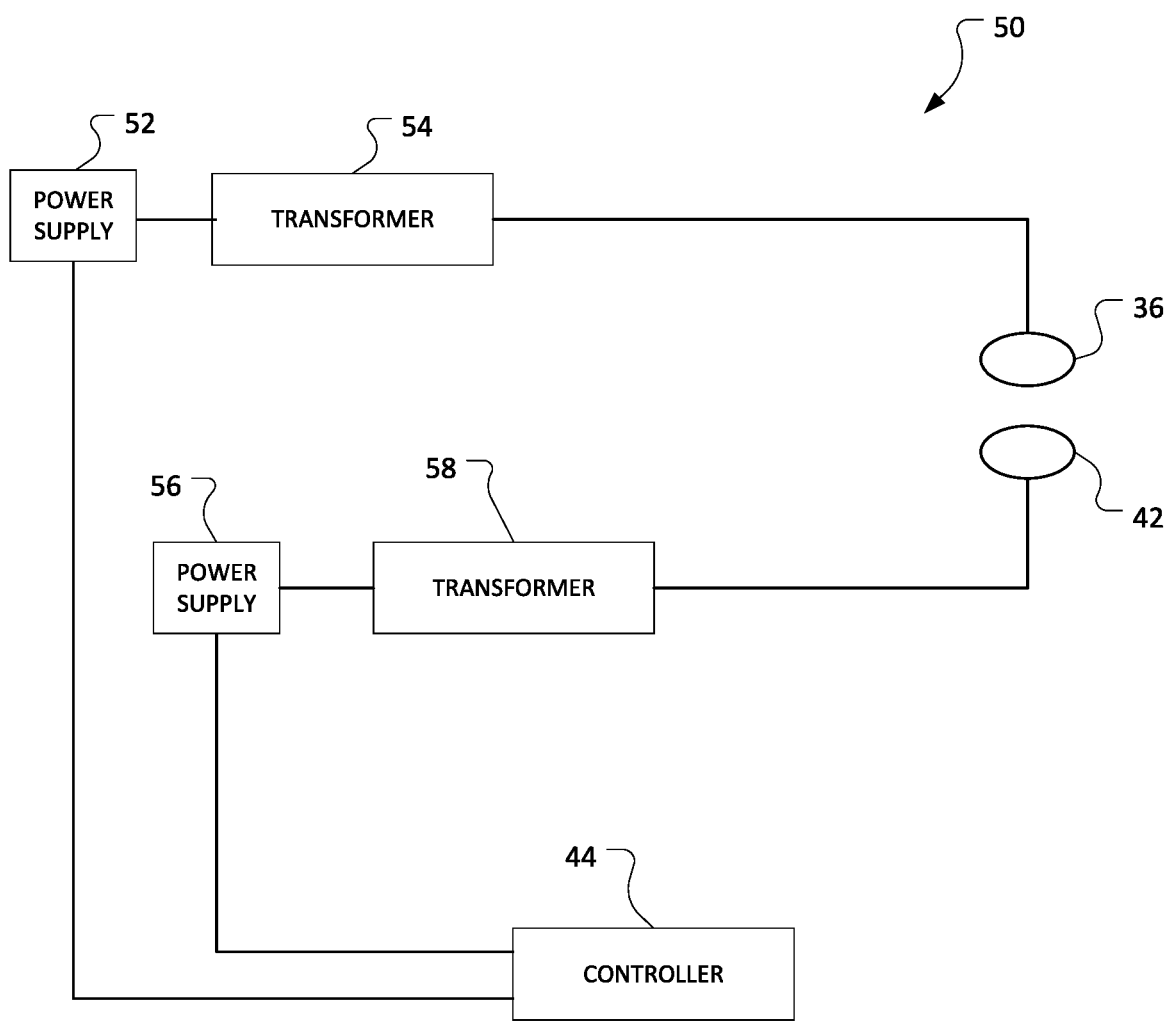
FIG. 4 shows an alternative embodiment of a kilohertz transcranial magnetic perturbation, temporal interference system.

FIG. 4 shows an alternative embodiment of the multi-coil system 50. As a further simplification of the system, instead of having frequency synthesizers and amplifiers that deliver separate frequencies to each coil, coil 36 could have its own power supply 52 and transformer 54 to deliver a first frequency. Similarly, coil 42 could have its own power supply 56 and transformer 58 to deliver a second frequency. The transformers would establish different frequencies in the currents produced in the coils, resulting in temporal interference at a fixed frequency. The controller 44 may have a simpler architecture, may provide the current control between the two coils, but may be optional. It is also possible that the same power supply could provide the incoming power to the two transformers that would operate to control the frequency delivered to each coil. In that instance, one power supply would be eliminated and the other power supply would move down in front of or as part of the controller.

In the above embodiments, each coil has a power source, either a power supply or a voltage to current source, either as individual power source or shared. Each coil has a corresponding frequency controller, either in the form of a frequency synthesizer, when the power source is a voltage to current source, or a transformer, when the power source is a power supply. The embodiment having transformers may have corresponding power supplies for each coil, or may have one power supply that provides power to two or more coils.

The temporal interference allows the focal location to be moved by control of the current distribution between the coils. For example, the current applied to each coil may be adjusted to cause the focal location of the perturbation to be nearer one coil or the other, allowing the location to be moved without any extra equipment system, and moved quickly, very important in the diagnostic environment where a human subject has to hold still. The changes in the current are very small, as are the differences in the frequencies, as discussed above. The differences may be adjusted by a percentage difference rather than parameters such as voltage, current or frequency.

It is well known that despite which method is used the electric field within the head cannot contain true extrema. The extreme values are found on the boundaries of the head; that is, the scalp surface. Therefore, when designing new systems to perturb brain function, it is of considerable importance to understand with some generality the characteristics of the brain and scalp electric fields of each method. In addition, it is important for the researcher to understand the energetic costs of generating electric fields by each method.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the embodiments.

What is claimed is:

1. A magnetic stimulation system, comprising:
at least two magnetic coils, each coil to generate an electric field of a magnitude having a desired effect on a brain;
at least two frequency controllers, wherein each coil is electrically connected to a corresponding frequency controller, the frequency controllers to adjust a frequency of power supplied to the corresponding coils according to a desired interference pattern;
at least one power source to provide power to the frequency controllers corresponding to each coil; and a controller to control the at least one power source and the frequency controllers corresponding to each coil to apply continuous current waveforms to each coil according to the desired interference pattern between the at least two coils.

2. The magnetic stimulation system as claimed in claim 1, wherein the at least two frequency controllers comprise frequency synthesizers and the at least one power source comprises at least two voltage to current sources, each coil having a corresponding voltage to current source.

3. The magnetic stimulation system as claimed in claim 1, wherein the controller is configurable to operate the coils with amplitude modulation.

4. The magnetic stimulation system as claimed in claim 1, wherein the controller is configurable to operate the frequency controllers at different frequencies.

5. The magnetic stimulation system as claimed in claim 1, wherein the at least two frequency controllers and the at least one power source comprise at least two transformers establishing a fixed interference pattern, and the at least one power source comprises a power supply.

6. The magnetic stimulation system as claimed in claim 1, wherein the magnetic coils are one of circular or figure-8 or a geometry appropriate to generation of a focal electric field response in the brain.

7. A method of operating a magnetic stimulation system, comprising:
generating two or more different signals to apply to two or more coils using frequency controllers corresponding to each coil, the frequency controllers to adjust a frequency of power supplied to the corresponding coils according to a desired interference pattern; and
using a controller to control at least one power source providing power to the two or more coils and the frequency controllers corresponding to each coil, and to apply continuous current waveforms to each coil according to the desired interference pattern between the two or more coils.

8. The method as claimed in claim 7, wherein the different signals differ in frequency by a percentage of a carrier frequency.

9. The method as claimed in claim 7, wherein generating the two or more different signals comprises generating temporal interference at a desired frequency.

10. The method as claimed in claim 9, wherein generating temporal interference signals comprises controlling the frequency of the two or more signals to adjust a focal location of magnetic energy.

11. The method as claimed in claim 7, wherein generating the two or more signals comprises:
using the controller to provide a signal to the frequency controllers to generate two or more different signals as two or more signals of different frequencies; and
sending each of the two or more signals of different frequencies to a corresponding voltage to current source connected to each of the two or more coils.

12. The method as claimed in claim 7, wherein generating the two or more different signals comprises:
using at least two transformers, each transformer corresponding to one of the two or more coils, each transformer to control the frequency of one of the two or more signals sent to each of the corresponding coils according to a desired temporal interference pattern between the at least two coils.

* * * * *